US008246949B2

(12) United States Patent
Higuchi et al.

(10) Patent No.: US 8,246,949 B2
(45) Date of Patent: Aug. 21, 2012

(54) METHODS AND DEVICES FOR SUSTAINED IN-VIVO RELEASE OF AN ACTIVE AGENT

(75) Inventors: John Higuchi, Salt Lake City, UT (US);
S. Kevin Li, Salt Lake City, UT (US);
William I. Higuchi, Salt Lake City, UT (US); Matthew S. Hastings, Midvale, UT (US)

(73) Assignee: Aciont, Inc., Salt Lake City, UT (US)

( * ) Notice: Subject to any disclaimer, the term of this patent is extended or adjusted under 35 U.S.C. 154(b) by 982 days.

(21) Appl. No.: 11/238,144

(22) Filed: Sep. 27, 2005

(65) Prior Publication Data

US 2006/0088515 A1    Apr. 27, 2006

Related U.S. Application Data

(60) Provisional application No. 60/623,150, filed on Oct. 27, 2004.

(51) Int. Cl.
*A61K 38/43* (2006.01)
*A61K 47/36* (2006.01)
*A61K 31/74* (2006.01)

(52) U.S. Cl. .............. 424/94.1; 424/78.04; 604/20

(58) Field of Classification Search .............. None
See application file for complete search history.

(56) References Cited

U.S. PATENT DOCUMENTS

| | | | |
|---|---|---|---|
| 4,627,879 A * | 12/1986 | Rose et al. | 106/124.1 |
| 4,738,850 A * | 4/1988 | Thakur et al. | 424/468 |
| 5,246,417 A | 9/1993 | Haak et al. | |
| 5,252,318 A * | 10/1993 | Joshi et al. | 424/78.04 |
| 5,298,017 A | 3/1994 | Theeuwes et al. | |
| 5,334,138 A | 8/1994 | Sage | |
| 5,443,505 A | 8/1995 | Wong et al. | |
| 5,496,266 A * | 3/1996 | Haak et al. | 604/20 |
| 5,605,536 A | 2/1997 | Sibalis | |
| 5,766,242 A | 6/1998 | Wong et al. | |
| 5,824,072 A | 10/1998 | Wong | |
| 5,958,443 A * | 9/1999 | Viegas et al. | 424/427 |
| 6,154,671 A | 11/2000 | Parel et al. | |
| 6,319,240 B1 | 11/2001 | Beck | |
| 6,331,313 B1 | 12/2001 | Wong et al. | |
| 6,394,994 B1 * | 5/2002 | Vilambi et al. | 604/501 |
| 6,442,423 B1 | 8/2002 | Domb et al. | |
| 6,539,251 B2 | 3/2003 | Beck et al. | |
| 6,579,276 B2 | 6/2003 | Lloyd et al. | |
| 6,697,668 B2 | 2/2004 | Parkinson et al. | |
| 6,699,493 B2 | 3/2004 | Wong | |
| 2002/0107503 A1 * | 8/2002 | Gordon | 604/507 |
| 2002/0183685 A1 | 12/2002 | Crawford et al. | |
| 2003/0023228 A1 | 1/2003 | Parkinson et al. | |
| 2003/0195403 A1 | 10/2003 | Berner et al. | |
| 2003/0203849 A1 | 10/2003 | Araki et al. | |
| 2004/0071761 A1 * | 4/2004 | Miller et al. | 424/449 |
| 2004/0167459 A1 | 8/2004 | Higuchi et al. | |
| 2004/0267188 A1 | 12/2004 | Behar et al. | |
| 2005/0009910 A1 * | 1/2005 | Hughes et al. | 514/559 |
| 2005/0181018 A1 | 8/2005 | Peyman | |
| 2006/0110428 A1 | 5/2006 | deJaun et al. | |

FOREIGN PATENT DOCUMENTS

| | | | |
|---|---|---|---|
| GB | 2 239 803 | | 7/1991 |
| WO | WO 00/02564 | | 1/2000 |
| WO | WO 03/030989 | | 4/2003 |
| WO | WO 03/039622 | | 5/2003 |
| WO | WO 03/043689 | | 5/2003 |
| WO | WO 03/089008 | * | 10/2003 |
| WO | WO 2004/050060 | * | 6/2004 |
| WO | WO 2004/105864 | | 12/2004 |

OTHER PUBLICATIONS

Prausnitz, Mark R.; Advanced Drug Delivery Reviews, 2004, vol. 56, pp. 581-587.*
Webster's New World College Dictionary, 2005, Wiley Publishing, Inc., http://www.yourdictionary.com/soluble?print pp. 1-2.*
Parkinson et al., "Tolerance of Ocular Iontophoresis in Healthy Volunteers", Journal of Ocular Pharmacology and Therapeutics, 2003, vol. 19, No. 2, pp. 145-151.*
Vollmer, D.L. et al., "Transscleral Iontophoretic Delivery of an Anti-Tumor Vascular Targeting Agent Combretastatin to Rabbit Eyes", Invest Ophthalmol Vis Sci., 2002; vol. 43: E-Abstract 3873.
U.S. Appl. 11/238,104, filed Sep. 27, 2005, Higuchi et al. Office Action issued Sep. 11, 2008.
U.S. Appl. No. 11/238,104, filed Sep. 27, 2005 John W. Higuchi. Office action issued Apr. 1, 2009.
U.S. Appl. No. 11/238,104, filed Sep. 27, 2005, John Higuchi. Office action issued Oct. 29, 2009.
H. Mollman et al. "Pharmacokinetics of Triamcinolone Acetonide and Its Phosphate Ester". Eur J Clin Pharmacol (1985) 29: 85-89.
PostScript. Br J Ophthalmol 2002; 86: 1063-1069. pp. 1063-1069. www.bjophthalmol.com.
U.S. Appl. No. 11/827,373, filed Jul. 10, 2007, John W. Higuchi. Office action issued Mar. 5, 2010.
U.S. Appl. No. 11/827,373, filed Jul. 10, 2007, John W. Higuchi, Office action issued Sep. 23, 2010.
Filho, Morizot Leite, "Use of Triamcinolone Acetonide Phosphate and Its Combination With Neomycin and Gramicidin in Opthamology" [Emprego do fosfato de acetonil triamcinolona e sua associacao a neomicina e gramicidina em oftalmologia], A Folha Medica, Jul. 1965, vol. 51, No. 1, pp. 13-20, English summary on p. 20.

* cited by examiner

*Primary Examiner* — L J Schuberg
(74) *Attorney, Agent, or Firm* — Thorpe North & Western LLP

(57) ABSTRACT

The present invention includes methods and devices for providing sustained in-vivo release of an active agent to a subject. In some aspects, such release may be achieved by reacting an active agent in-vivo with a depot forming agent in order to form a sustained release active agent depot inside the subject. The depot can then release the active agent over a sustained period of time.

33 Claims, 2 Drawing Sheets

METHODS AND DEVICES FOR SUSTAINED IN-VIVO RELEASE OF AN ACTIVE AGENT

PRIORITY DATA

This application claims the benefit of U.S. Provisional Patent Application Ser. No. 60/623,150, filed on Oct. 27, 2004, which is incorporated herein by reference.

FIELD OF THE INVENTION

The present invention relates to systems, methods, and devices for in-vivo sustained release of an active agent following minimally invasive or noninvasive delivery thereof through a localized region of an individual's body tissue, particularly the eye. Accordingly, the present invention involves the fields of chemistry, pharmaceutical sciences, and medicine, particularly ophthalmology.

BACKGROUND OF THE INVENTION

Posterior and intermediate eye diseases that require ocular drug delivery to prevent blindness include uveitis, bacterial and fungal endophthalmitis, age-related macular degeneration, viral retinitis, and diabetic retinopathy, among others. For example, the reported incidence of posterior uveitis is more than 100,000 people in the United States. If left untreated, uveitis leads to blindness. It is responsible for about 10 percent of all visual impairment in the U.S. and is the third leading cause of blindness worldwide.

Treatments of intermediate and posterior uveitis are complicated by the inaccessibility of the posterior eye to topically applied medications. Current therapy for intermediate and posterior uveitis requires repeated periocular injections and/or high-dose systemic therapy with corticosteroids. Injections are usually preferred to systemic drug administration because the blood/retinal barrier impedes the passage of most drugs from the systemically circulating blood to the interior of the eye. Therefore large systemic doses are needed to treat intermediate and posterior uveitis, which often result in systemic toxicities including immunosuppression, adrenal suppression, ulcerogenesis, fluid and electrolyte imbalances, fat redistribution and psychological disorders.

Endophthalmitis affects approximately 10,000 people in the United States each year. Endophthalmitis is typically caused by gram-positive bacteria after ocular surgery or trauma, but it can also be fungal or viral in nature. The current method of treating endophthalmitis is direct injection of antimicrobials into the vitreous. Intravitreal injections are necessary because periocular injections and systemic administration do not deliver efficacious amounts of antibiotics to the target sites in the eye. Age-related macular degeneration (AMD) is the leading cause of irreversible loss of central vision in patients over the age of 50. AMD affects more than 15 million people worldwide.

Treatments of posterior eye diseases require intravitreal and periocular injections or systemic drug administration. Systemic administration is usually not preferred because of the resulting systemic toxicity as discussed above. While intravitreal and periocular injections are preferable to systemic administration, the half-life of most injected compounds in the vitreous is relatively short, usually on the scale of just a few hours. Therefore, intravitreal injections require frequent administration. The repeated injections can cause pain, discomfort, intraocular pressure increases, intraocular bleeding, increased chances for infection, and the possibility of retinal detachment. The major complication of periocular injections is accidental perforation of the globe, which causes pain, retinal detachment, ocular hypertension, and intraocular hemorrhage. Other possible complications of periocular injections include pain, central retinal artery/vein occlusion, and intraocular pressure increases. Therefore, these methods of ocular drug delivery into the posterior of the eye have significant limitations and major drawbacks. In addition, injections are very poorly accepted by patients. These methods also involve high healthcare cost due to the involvement of skilled and experienced physicians to perform the injections.

Ocular iontophoresis is a noninvasive technique used to deliver compounds of interest into the interior of a patient's eye. In practice, two iontophoretic electrodes are used in order to complete an electrical circuit. In traditional, transscleral iontophoresis, at least one of the electrodes is considered to be an active iontophoretic electrode, while the other may be considered as a return, inactive, or indifferent electrode. The active electrode is typically placed on an eye surface. The compound of interest is transported at the active electrode across the tissue when a current is applied to the electrodes through the tissue. Compound transport may occur as a result of a direct electrical field effect (e.g., electrophoresis), an indirect electrical field effect (e.g., electroosmosis), electrically induced pore or transport pathway formation (electroporation), or a combination of any of the foregoing. Examples of currently known iontophoretic devices and methods for ocular drug delivery may be found in U.S. Pat. Nos. 6,319,240; 6,539,251; 6,579,276; 6,697,668, and PCT Publication Nos. WO 03/030989 and WO 03/043689, each of which is incorporated herein by reference.

Despite its apparent advantages, iontophoresis is really just a method of limiting the invasiveness of drug transport into the globe's interior. Once inside the eye, the pharmacokinetics of water soluble compounds are identical to those following intravitreal injections i.e. their half-lives are on the order of a few hours. Therefore, in many cases, traditional iontophoresis must be repeated as frequently as intravitreal injections, leading to patient inconvenience, increased costs, and increased possibility of untoward effects caused by the iontophoretic treatment itself.

Various techniques have been proposed to provide sustained release of a compound in the eye for the treatments of intermediate and posterior eye diseases. For example, the implantation of biodegradable polymers within the eye is disclosed and discussed in U.S. Pat. Nos. 5,443,505; 5,766, 242; 5,824,072; 6,331,313; and 6,699,493, each of which is incorporated herein by reference. While potentially effective, these methods are invasive, and therefore pose a high degree of risk and discomfort to the patient.

The issue with respect to dosing frequency is an issue that not only plagues treatment of ocular diseases, but is problematic for most other pharmacotherapy regimens. Most regimens of oral dosage formulations must be administered at least one a day, and often multiple times per day. Most topical dosing regimens also share this problem and require a daily application of the topical formulation. While transdermal patches can allow regimens with much less frequent dosing, transdermal patches suffer from other issues because of the fact that they are worn on the skin, such as visibility to others, skin irritation, and delamination issues. Furthermore, even with their potential to provide long term drug delivery, because of the skin irritation and delamination issues, the longest lasting patches currently on the market typically only last for 7 days and more often only last for 3-4 days before a new patch must be administered.

As such, devices, systems, and methods which are capable of minimally invasively, or non-invasively delivering drugs, particularly to the interior of the eye, without the need for frequent administration continue to be sought.

SUMMARY OF THE INVENTION

Accordingly, the present invention provides systems, devices, and methods of providing sustained in-vivo release of an active agent in a subject, with only minimal to noninvasiveness. In one aspect, such a method may include delivering the active agent to the subject, reacting the active agent with a depot forming agent inside the subject to precipitate the active agent and create an active agent sustained release depot, and allowing the depot to release the active agent over a sustained period of time. Exemplary reactions that can be used in order to create the sustained release depot may include without limitation, ionic associations between the active agent and the depot forming agent, reactions that cleave a portion of the active agent and thus lower its aqueous solubility, and induction of physiological environment influences that cause formation of a depot, or an effective depot (i.e. create a sustained release effect) among others. In many cases, the formation of the sustained release depot may be through in-vivo precipitation of the active by any of the above-recited mechanisms or another mechanism.

One important aspect of the present invention is that the active agent and depot forming agent are separately administered to the subject. In other words, they are not in physical contact with one another when delivered, such as in a mixed solution or suspension. However, it should be noted, that while the active agent and depot forming agents are not delivered in physical contact with one another, they may in some aspects be delivered from the same device. Furthermore, such agents may be administered at the same time, through the same route, or at different times and through different routes, as long as they react in-vivo to form the sustained release depot.

In some aspects, the depot forming agent may be an endogenous substance of the subject's body, and though it can be administered, in some cases need not be. In this instance, only the active agent would be delivered.

The particular active agent to be delivered may be a variety of substances depending on the particular treatment to be effected. Such substances may include drugs in various forms, including prodrugs thereof, as required in order to provide convenient and effective minimally invasive, or non-invasive delivery, followed by formation of the sustained release depot in-vivo. Exemplary active agents are enumerated further herein.

Likewise, a variety of depot forming agents may be used in order to facilitate the formation of the in-vivo sustained release depot. Considerations in selecting a specific depot forming agent may include without limitation, the particular active agent being used, the physiologic area and type of administration, and the other ingredients to be included in the delivery formulation. Examples of specific depot forming agents that may be used are further enumerated herein.

In yet another aspect, the formation of the in-vivo depot may be aided by immobilizing the active agent in the subject's body. Immobilization thusly may prevent the active agent from circulating to other portions of the body before the sustained release depot is formed. A number of mechanisms for immobilizing the active agent can be used and will be recognized by those of ordinary skill in the art, such as the use of vasoconstrictors to constrict blood vessels in the vicinity of delivery. Similar mechanisms can be used to immobilize the depot forming agent in the subject's body.

In addition to the methods for forming an in-vivo sustained release depot, the present invention additionally encompasses a medicinal depot formulation in a subject formed by the methods articulated herein. In one aspect, such a depot may include a mass of active agent in precipitated form which becomes solubilized and releases active agent over a sustained period of time.

The present invention additionally encompasses devices for administration of an active agent and a depot forming agent which can be used to carry out the methods recited herein. In one aspect, such a device for providing sustained in-vivo release of an active agent in a subject may include a first electrode assembly configured to contain an active agent, and a second electrode assembly configured to contain a depot forming agent, the first and second electrodes having a distance from one another that controls the location of a sustained release depot formed in-vivo when used to deliver the active agent and the depot forming agent to the subject.

Additionally, the present invention encompasses methods of delivering a sustained release depot of an active agent to a specific location in a subject. In one aspect, such a method may include positioning a first electrode assembly containing the active agent on a body surface of the subject, and positioning a second electrode assembly containing a depot forming agent on an area of a body surface of the subject at an inter-electrode distance from the first electrode that dictates the location of the depot formation within the subject.

The present invention additionally includes methods of treating various conditions and diseases using the devices, systems, and methods recited herein. In one particular aspect, such a condition or disease may be an ocular condition or disease. Examples of such conditions include without limitation, macular edema, age related macular degeneration, anterior, intermediate, and posterior uveitis, HSV retinitis, diabetic retinopathy, bacterial, fungal, or viral endophthalmitis, eye cancers, glioblastomas, glaucoma, and glaucomatous degradation of the optic nerve.

DETAILED DESCRIPTION OF THE INVENTION

Figure 1:
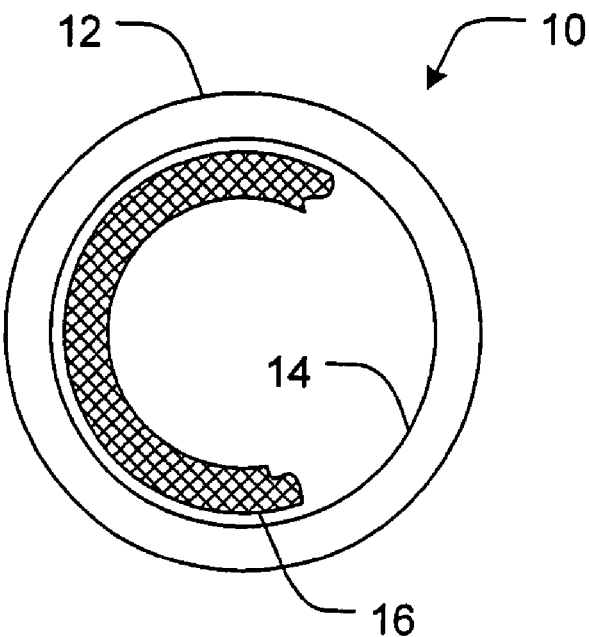
FIG. 1 is a front view of an iontophoretic device in accordance with an aspect of the present invention.

Before the present systems and methods for sustained release ocular drug delivery are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and, "the" include plural referents unless the context clearly dictates otherwise. Thus, for example, reference to "a polymer" includes reference to one or more of such polymers, and "an excipient" includes reference to one or more of such excipients.

DEFINITIONS

In describing and claiming the present invention, the following terminology will be used in accordance with the definitions set forth below.

As used herein, "formulation" and "composition" may be used interchangeably herein, and refer to a combination of two or more elements, or substances. In some embodiments a composition may include an active agent, an excipient, or a carrier to enhance delivery or depot formation.

As used herein, "active agent," "bioactive agent," "pharmaceutically active agent," and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical, and medicinal arts. Examples of drugs useful in the present invention include without limitation, steroids, antibacterials, antivirals, antifungals, antiprotozoals, antimetabolites, immunosuppressive agents, VEGF inhibitors, ICAM inhibitors, antibodies, protein kinase C inhibitors, chemotherapeutic agents, neuroprotective agents, nucleic acid derivatives, aptamers, proteins, enzymes, peptides, and polypeptides.

As used herein "prodrug" refers to a molecule that will convert into a drug (its commonly known pharmacological active form). Prodrugs themselves can also be pharmacologically active, and therefore are also expressly included within the definition of an "active agent" as recited above. For example, dexamethasone phosphate can be classified as the prodrug of dexamethasone, and triamcinolone acetonide phosphate can be classified as a prodrug of triamcinolone acetonide.

As used herein, "effective amount," and "sufficient amount" may be used interchangeably and refer to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein, "sclera" refers to the sclera tissue in the eye or the conjunctiva between the limbus and the formix on the surface of the eye, which is the white part of the eye. "Sclera" is also used in referring to other eye tissues.

As used herein, "subject" refers to a mammal that may benefit from the administration of a composition or method as recited herein. Most often, the subject will be a human but can be of other animals such as dogs and cats.

As used herein, "administration," and "administering" refer to the manner in which an active agent, or composition containing such, is presented to a subject. As discussed herein, the present invention is primarily concerned with iontophoretic delivery, especially with occular delivery.

As used herein, "noninvasive" refers to a form of administration that does not rupture or puncture a biological membrane or structure with a mechanical means across which a drug or compound of interest is being delivered. A number of noninvasive delivery mechanisms are well recognized in the transdermal arts such as patches, and topical formulations. Many of such formulations may employ a chemical penetration enhancer in order to facilitate non-invasive delivery of the active agent. Additionally, other systems or devices that utilize a non-chemical mechanism for enhancing drug penetration, such as iontophoretic devices are also known. "Minimally invasive" refers to a form of administration that punctures a biological membrane or structure but does not cause excessive discomfort to the subjects and severe adverse effects. Examples of "minimally invasive" drug delivery are microneedle, laser, or heat punctuation in transdermal delivery and periocular injections in ocular delivery.

As used herein, "depot" refers to a temporary mass inside a biological tissue or system, which includes a drug that is released from the mass over a period of time. In some aspects, a depot may be formed by the interaction of an active agent with a depot forming agent, such as a complexing ion which will form an active agent complex that is less soluble than the active agent by itself, and thus precipitate in-vivo.

As used herein, the term "body surface" refers to an outer tissue surface of the subject such as tissue surfaces encountered in ocular and transdermal delivery, or mucosal tissues lining a body cavity such as the mouth for buccal delivery or vaginal tract for vaginal delivery. The term "skin" refers to an outer tissue surface of the subject. It is therefore intended that skin also refer to mucosal and epithelial tissues, as well as the outer surfaces of the eye.

As used herein, the term "electrode assembly" refers to an assembly of at least one electrode and at least one reservoir.

As used herein, the term "reservoir" refers to a body or a mass that may contain a depot forming agent or an active agent. As such, a reservoir may include any structure that may contain a liquid, as well as solid structures made up of the agent to be delivered. In some cases, an electrode may be considered to be a reservoir.

As used herein, the term "reacting" refers to any force, change in environmental conditions, presence or encounter of other chemical agent, etc. that alters the active agent. For example, "reacting" between the active agent and the depot forming agent can be physical or chemical interactions.

As used herein, the term "precipitate" refers to anything less than fully solubilized. As such, a precipitate can include not only crystals, but also gels, semi-solids, increased molecular weight, etc.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

THE INVENTION

The present invention provides methods, devices, and formulations for forming in-vivo a sustained release depot in a subject. Such a depot may be created inside the tissue or in an organ of the subject, from which a therapeutic agent is released on a sustained basis. One example of an organ where such an administration method may be beneficial is the eye. It should be noted, however, that it is intended that the scope of the present claims cover all tissues where aspects of the present invention may be effectively carried out.

In one aspect the sustained release depot may be formed by the reaction of an active agent with a depot forming agent in a body tissue, for example an organ such as the eye, following delivery of the active agent to the subject. The delivery of the active agent may be by any noninvasive or minimally invasive means known, and may include active delivery or passive delivery. The depot forming agent may also be delivered to the subject, or it may be an endogenous substance that reacts with the active agent. In either case, the depot forming agent and the active agent do not interact with one another until the active agent is delivered into the subject. As such, in most cases the active agent and the depot forming agent will be separated until both are located in-vivo. If the depot forming agent is to be delivered to the subject, then both agents should be delivered separately. Endogenous depot forming agents will, of course, not come into contact with the active agent until administration occurs. Thus an in-vivo reaction between the active agent and the depot forming agent will cause the active agent or a derivative thereof to form a depot. In one aspect such a depot forming mechanism may be a change in the solubility of the active agent, thus causing precipitation and subsequent depot formation. This depot of active agent complex is then able to deliver a therapeutic compound to the biological system over time. Such sustained delivery can include local or systemic delivery of the active agent to the subject. As such, in one embodiment, a depot forming agent may be created at a desired location in a subject, and the active agent may be systemically administered and may "collect" at the depot forming agent to form a depot as the active agent circulates through the body. In another aspect, the depot forming agent may not react directly with the active agent, but still functions to facilitate the formation of a sustained release depot. In such a case, the depot forming agent may react with an area of a local environment to cause an alteration therein. The active agent would then react with the altered area of the local environment to form a depot as a result of the changes facilitated by the depot forming agent.

As a sustained release mechanism, it will be recognized that the depot formulation of the present invention generally has an in-vivo solubility that is lower than that of the active agent by itself. In this way, as the active agent dissolves out of the depot over time, a sustained therapeutic effect may be obtained. Further, since the active agent in the depot is unable to have a therapeutic effect until released therefrom, the solubility properties of the depot limit potential toxicity or overdose concerns that would normally arise when delivering a sufficient amount of drug to last over a prolonged period.

In a detailed aspect, one method in accordance with the present invention may include: a) delivering an active agent to the subject to a localized physiologic region, for example in an organ such as the eye, using iontophoresis; b) reacting the active agent with a depot forming agent inside the subject to precipitate the active agent and create an active agent sustained release depot; and c) allowing the depot to release the active agent over a sustained period of time. The rate of drug release is related to the solubility of the depot and follows a diffusion-controlled process. This method is particularly suited for iontophoretic transport of a therapeutic compound and sustaining its level in the eye by means of sustained release of the compound in the eye for the treatment of anterior, intermediate, and posterior eye disease. In addition to iontophoresis, the active agent may be delivered by any means known to one of ordinary skill in the art, including sonophoresis, electroporation, passive diffusion, etc.

In another aspect, a method of providing non-invasive drug delivery with subsequent sustained release of the delivered drug to subject may include forming a depot of an active agent in the subject by non-invasively administering the active agent and a depot forming agent to the subject, and allowing release of the active agent from the depot over a period of time.

Though numerous conditions would benefit from the methods and devices of the present invention, they are particularly well suited for the treatment of ocular diseases such as direct, combinatory, and adjunctive therapies. This is because of the relatively high permeability of the eye tissues and the large aqueous compartments in the eye. Examples of eye diseases include without limitation, macular edema, age related macular degeneration, anterior, intermediate, and posterior uveitis, HSV retinitis, diabetic retinopathy, bacterial, fungal, or viral endophthalmitis, eye cancers, glioblastomas, glaucoma, and glaucomatous degradation of the optic nerve. Additionally, skin diseases such as herpes, cancer, and psoriasis may be effectively treated by the various aspects described herein. Other conditions that would benefit from the methods and devices of the present invention are diseases that can be benefited from local and systemic transdermal delivery such as in the treatments of pain and muscle and joint inflammation.

For effective sustained release in the tissues surrounded by blood circulation such as the conjunctiva, uvea, and sclera, the depot should have low aqueous solubility. The aqueous solubility of the active agent is preferred to be below $10^{-4}$ M or the solubility product (Ksp) is preferred to be below $10^{-8}$ $M^2$ for a 1:1 active agent to depot forming agent complex to achieve sustained release of at least approximately one day. The solubility of the depot complex should not be too high for long sustained release of the active agent and not too low to provide a therapeutic effect. The preferred solubility of the active agent is in the range from $10^{-12}$ to $10^{-4}$ M depending on the physicochemical properties and therapeutic actions of the active agent compound. The solubility of the active agent or the depot complex is not the only sustained release parameter. The rate of active agent release is also related to the amount of active agent deposited in the tissue, which can be controlled by the delivery method such as iontophoresis, for a desired rate of active agent release. Other parameters that affect the release of the active agent compounds are the diffusion coefficient of the active agent in the tissue, the porosity of the tissue, the tortuosity of the tissue, and the clearance of the blood vasculature. An external means such as heat and vibration can also be used to facilitate the rate of release. In addition, the formation of the depot complex should occur rapidly to prevent pre-complexation clearance of the active agent or the depot forming agent. The depot forming agent and active agent concentrations required for the nucleation of the depot should be low.

In use, the depot forming agent may act to lower the aqueous solubility of the active agent. By altering the solubility properties thusly, the active agent is caused to precipitate in-vivo and form a depot of the agent which can then release drug to the subject over an extended period of time. A variety of mechanisms for lowering the solubility of the active agent may be used. In one aspect, the depot forming agent may form a complex with the active agent that has a solubility that is lower than that of the active agent by itself.

A wide range of active agents may be used in the present invention as will be recognized by those of ordinary skill in the art. In fact, nearly any agent that can react with a depot forming agent in-vivo to form a depot may be used. Examples of the active agents that may be used in the treatment of various conditions include, without limitation, analeptic agents, analgesic agents, anesthetic agents, antiasthmatic agents, antiarthritic agents, anticancer agents, anticholinergic agents, anticonvulsant agents, antidepressant agents, antidiabetic agents, antidiarrheal agents, antiemetic agents, antihelminthic agents, antihistamines, antihyperlipidemic agents, antihypertensive agents, anti-infective agents, antiinflammatory agents, antimigraine agents, antineoplastic agents, antiparkinsonism drugs, antipruritic agents, antipsychotic agents, antipyretic agents, antispasmodic agents, antitubercular agents, antiulcer agents, antiviral agents, anxiolytic agents, appetite suppressants, attention deficit disorder and attention deficit hyperactivity disorder drugs, cardiovascular agents including calcium channel blockers, antianginal agents, central nervous system ("CNS") agents, beta-blockers and anti-arrhythmic agents, central nervous system stimulants, diuretics, genetic materials, hormonolytics, hypnotics, hypoglycemic agents, immunosuppressive agents, muscle relaxants, narcotic antagonists, nicotine, nutritional agents, parasympatholytics, peptide drugs, psychostimulants, sedatives, steroids, smoking cessation agents, sympathomimetics, tranquilizers, vasodilators, β-agonists, and tocolytic agents, and mixtures thereof.

Additionally, further examples of active agents may include steroids, aminosteroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides and mixtures thereof. Specific examples of useful antiviral active agents include acyclovir or derivatives thereof.

Specific examples of active agents may also include hydromorphone, dexamethasone phosphate, amikacin, oligonucleotides, Fab peptides, PEG-oligonucleotides, salicylate, tropicamide, methotrexate, 5-fluorouracil, squalamine, triamcinolone acetonide, diclofenac, combretastatin A4, mycophenolate mofetil, mycophenolic acid, and mixtures thereof.

Under a number of circumstances, the active agent used may be a prodrug, or in prodrug form. Examples of advantageous use of a prodrug may include when the drug itself does not properly interact with the depot forming agent to form a depot, or when an even lengthier administration period is desired, among others. Prodrugs for nearly any desired active agent will be readily recognized by those of ordinary skill in the art. Additionally, prodrugs with high electromobility which metabolize into drugs with a low aqueous solubility may be advantageously used as both the drug and the depot forming agent. In this case, the prodrug may be iontophoretically delivered and then precipitate into a depot in-vivo upon the metabolism (e.g. enzymatic cleavage) of the prodrug into the drug.

Though any prodrug capable of forming a depot would be considered to be within the scope of the present invention, examples may include the derivatives of steroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides, and mixtures thereof. One specific example of a steroid derivative may include triamcinolone acetonide phosphate or other derivatives of triamcinolone acetonide, dexamethasone phosphate. For example, it may be preferable to label a steroid with one or more phosphate, sulfate, or carbonate functional groups, so the prodrug can be effectively delivered into the eye and form a complex with the precipitating ion.

In yet another aspect, an electrically mobile prodrug of a low solubility drug in iontophoresis can be used to create a sustained release system in the eye. Because the prodrug has high electromobility, it is effectively delivered into the eye. The prodrug then converts into the low solubility drug in the eye and the insoluble drug precipitates in the eye. The drug in solid state in the eye will be slowly released into the eye and provide an ocular sustained release condition.

For a relatively high solubility drug, a prodrug with low solubility and a pro-prodrug with high electromobility can be used. The high electromobility pro-prodrug allows the effective iontophoretic delivery of the pro-prodrug. Once in the eye, the pro-prodrug is converted into a prodrug which is insoluble and precipitates in the eye. The conversion of the prodrug to the drug will slowly release the drug from the precipitate and provide a sustained release condition.

Various reactions are contemplated that result in a sustained release depot being formed. The reaction between the active agent and the depot forming agent may include an ionic association. Accordingly, in one aspect the depot forming agent can have at least one opposite charge to at least one of the charged groups on the active agent. In another aspect, the depot forming agent can have more than one charge and will be capable of being juxtaposed with more than one charge on the active agent. In yet another aspect, the charges on the depot forming agent can be polyvalent, allowing more than one active agent ion to enter the depot complex. This allows stronger associations between complexing depot forming agents, thereby lowering the solubility constant of the depot complex, Ksp, thus increasing the duration of therapy. In one aspect, the depot forming agent may be an ion. Examples of useful depot forming agents include without limitation, $Ca^{2+}$, $Sn^{2+}$, $Fe^{2+}$, $Fe^{3+}$ $Mn^{2+}$, $Mg^{2+}$, $Zn^{2+}$, $NH_4^+$, ions of the transition metals in the periodic tables, $PO_4^{3-}$, $CO_3^{2-}$, $SO_4^{2-}$, organic cations, organic anions, polyvalent metals, chelation agents, and ionic pharmaceutical excipients generally used in the pharmaceutical industry or known to the people skilled in the art. The depot forming agents preferably have more than one charge for effective iontophoretic delivery and for effectively precipitating the active agent. In one aspect, the depot forming agent may have an adequate ionic charge for both effective iontophoretic delivery and effectively reacting with the active agent to form the sustained release depot.

The ratio of depot forming agent to active agent could be one to one. However, in the case of polyvalent depot forming agents, more than one active agent may complex with the same depot forming agent to form a depot complex. In one aspect, the depot complex may have a ratio of depot forming agent to active agent of from about 1:1 to about 1:4. In another aspect, the ratio may be about 1:1. In a further aspect, the ratio may be about 1:2. In yet another aspect, the ratio may be about 1:3. In yet a further aspect, the ratio may be about 1:4. In one more aspect, the ratio of depot forming agent to active agent may be from about 4:1 to about 1:4.

Two or more depot forming agents can be used at the same time to form the sustained release depot. With multiple depot forming agents, the concentration of each depot forming agent for precipitating the same total amount of active agent in the eye can be reduced. This effectively reduces the concentrations of the depot forming agent in the eye during and after delivery, so the depot forming agent concentrations are always below the levels that may cause adverse effects in the eye. The use of multiple depot forming agents also provides other advantages. For example, sustained release can be further controlled by using multiple depot forming agents that have different depot complex-Ksp values.

Other examples of depot forming agents may include, without limitation, catalysts, polymerization initiators, pegylating agents, solvents, pH, thermal, or ionic strength sensitive polymers, active agents used in the treatment of eye diseases, aminosteroids such as squalamine, derivatives of triamcinolone acetonide, and combinations and mixtures thereof.

Typically, the depot forming agent is non-toxic in the body and the eye. The solid depot complex should be non-toxic and should not cause any side effects in the eye. The formation of the depot complex should also occur rapidly to prevent pre-complexation clearance of the active agent or depot forming agent from the vitreous. Additionally, the depot forming agent and active agent concentrations required for the nucleation of the depot should be low. The depot complex has decreased solubility and is not cleared or has reduced clearance from the eye in its complex form. As such, the clearance of the depot forming agent and the active agent in the eye should be relatively slow compared with the precipitation process to allow the completion of depot formation.

In another aspect, the reaction process can result in depot complexes in the form of a gel or aggregation, and may alternatively be crystalline or amorphous in form. In this case, the gel should not create any unwanted side effects in the eye. For example, in one specific aspect the depot may be a gel created by a complex of an active agent such as triamcinolone acetonide phosphate and a depot forming agent such as $Ca^{2+}$ ion. In some aspects, the particulate size within the depot may be controlled or adjusted so as to determine the release rate of the drug. Additionally, in yet another aspect, the reaction process may be a result of the cleavage of a portion of the active agent, thus lowering the aqueous solubility of the active agent. One example of such a process may include the enzymatic cleavage of the active agent. As such, the depot forming agent would be the enzyme.

As has been discussed, in one aspect the depot forming agent may be an endogenous substance in the subject's body. Examples of such agents may include without limitation, various enzymes, ascorbate, lactate, citrate, various amino acids, calcium, magnesium, zinc, iron, chloride, fluoride, as well as ions found in the tissues and vitreous of the eye. In such cases, the presence of such a substance inside the body may be relied upon in order to form the depot and the active agent only will be delivered. Alternatively, such substances may be delivered to the body if they are not thought to be present in sufficient concentration to form a depot.

An example of the compound of interest is triamcinolone acetonide and its derivatives (prodrugs) such as triamcinolone acetonide phosphate. Triamcinolone acetonide can be obtained from the metabolism and hydrolysis of triamcinolone acetonide phosphate. Due to the low aqueous solubility of triamcinolone acetonide, the precipitation of triamcinolone acetonide in the tissue provides a sustained release system after the delivery of triamcinolone acetonide phosphate. However, triamcinolone acetonide phosphate may be cleared quickly from the delivery site and may not provide long enough residence in the tissue for the metabolism and hydrolysis of triamcinolone acetonide phosphate. In one aspect, triamcinolone acetonide phosphate can first be precipitated by a counterion in the tissue, which has higher aqueous solubility than that of triamcinolone acetonide. The triamcinolone acetonide phosphate-counterion complex has low enough solubility to provide tissue residence for triamcinolone acetonide phosphate-to-triamcinolone acetonide conversion. When triamcinolone acetonide phosphate is released from the precipitate depot, triamcinolone acetonide phosphate is converted to triamcinolone acetonide. The solubility of triamcinolone acetonide is low and will precipitate in the tissue to provide further sustained release capability. In another aspect, the precipitating process can result in ion-drug complexes in the form of a gel or aggregation. The gel or aggregation allows enzyme degradation and conversion to occur before drug clearance. Gel formation has been observed when dexamethasone phosphate (a prodrug of dexamethasone) or triamcinolone acetonide phosphate was mixed with calcium ions.

In some cases, it is not undesirable to have only a portion, even a small fraction of the total active agent delivered react with the depot forming agent during iontophoresis treatment. In such a case, a relatively high free active agent concentration in the eye as a result of ocular iontophoretic drug delivery provides a "burst" therapeutic effect in the first few hours (or days) after the initial iontophoretic treatment. After this initial "burst" treatment phase, the depot complex releases the active agent at a relatively slow rate and sustains a relatively low but therapeutic effective drug concentration in the eye for up to a few months after the initial treatment.

It may be beneficial for the application situs to be sealed with a sealant following delivery of the active agent and/or the depot forming agent. This procedure may protect the tissue in which iontophoretic administration occurred. Sealants may include any known to one of ordinary skill in the art, including gels, glues and impermeable polymeric or resinous membranes.

In some cases, depot formation may be hampered by the in-vivo movement of either the depot forming agent or the active agent in the eye. It is therefore contemplated that various means for restricting or slowing such movement may improve the effectiveness of depot formation. In one aspect, the in-vivo movement may be restricted by constriction of the blood vessels exiting an area in which active agent precipitation or other depot forming process occurs. Such constriction may be induced by the administration of a vasoconstricting agent. Such a vasoconstrictor may be administered actively by iontophoretic or other means, or it may be delivered passively. Specific non-limiting examples of vasoconstricting agents may include α-agonists such as naphazoline, and tetrahydrozoline, sympathomimetics such as phenylethylamine, epinephrine, norepinephrine, dopamine, dobutamine, colterol, ethylnorepinephrine, isoproterenol, isoetharine, metaproterenol, terbutaline, metearaminol, phenylephrine, tyramine, hydroxyamphetamine, ritrodrine, prenalterol, methoxyamine, albuterol, amphetamine, methamphetamine, benzphetamine, ephedrine, phenylpropanolamine, methentermine, phentermine, fenfluramine, propylhexedrine, diethylpropion, phenmetrazine, and phendimetrazine. Vasoconstricting agents can be administered either before or concurrently with the administration of the active agent. Though administration of the vasoconstrictor may occur following administration of the active agent, the results may be less effective than prior or concurrent administration. Additionally, in some aspects, the vasoconstricting agent may have the same polarity as the active agent and administered concurrently with the active agent. Similarly, the vasoconstricting agent may have the same polarity as the depot forming agent and administered with the depot forming agent.

In another aspect of the present invention, in-vivo movement may be restricted by constriction of blood vessels as a result of the application of physical force to the blood vessels.

Various aspects of the present invention are contemplated to encompass iontophoretic devices that function to form a sustained release depot. Accordingly, in one aspect a device for providing sustained in-vivo release of an active agent in a subject is described. Such a device may include a first electrode assembly configured to contain an active agent and a second electrode assembly configured to contain a depot forming agent. Each electrode assembly is made up of at least one reservoir and at least one electrode. These electrodes provide electrical current to the respective reservoirs, and thus iontophoretically drive the active agent and the depot forming agent into the subject. The distance between the first and second electrode assemblies may control the location of the sustained release depot formed in-vivo when the device is used to deliver the active agent and the depot forming agent to the subject.

In another aspect, a method for controlling the location of depot formation in a subject is described. The method may include positioning a first electrode assembly containing an active agent, and positioning a second electrode assembly containing a depot forming agent, the first and second electrode assemblies being positioned at an inter-electrode distance that controls a location of the depot formation.

Various device configurations are contemplated that allow the iontophoretic administration of an active agent and a depot forming agent through the tissue of a subject in order to form such a depot. For example, devices may be constructed wherein the first electrode assembly and the second electrode assembly are in an integrated single unit. In one aspect, the first electrode assembly and the second electrode assembly may be configured adjacent one another within the integrated single unit. Alternatively, devices may be constructed as a collection of separate electrode assemblies or arrays that function as a single unit. As such, in one aspect of the present invention, a device may be a single integral unit containing and delivering both the active agent and the depot forming agent. Such a device may have separate electrode assemblies, one to contain the active agent and one to contain the depot forming agent. Each of these electrode assemblies is placed in contact with the body surface though which the active agent and the depot forming agent are to be iontophoretically administered. In the case of ocular iontophoresis, the shape of the device may be configured to fit on an eye surface. In such a configuration, the electrode assemblies and their respective reservoirs may be in contact with various tissue structures in the eye, such as the conjunctiva. In one aspect, a portion of the device may cover the cornea with at least one reservoir being in contact with the conjunctiva. The portion covering the cornea provides a better fit of the device onto the eye. In another aspect, the device may extend into the cul-de-sac under the eyelids for the same purpose. The portion of the device in the cul-de-sac can also hold an electrode assembly or electrode assemblies in contact with the conjunctiva for administering either or both the active agent and the depot forming agent.

It may be beneficial to maintain the active agent and the depot forming agent in isolation from one another to prevent reaction within the device. Accordingly, the reservoirs of the electrode assemblies may be separated by a barrier made from an electrically inert material. This barrier should extend to the surface of the body surface, such as the eye surface, in order to minimize current flow between the reservoirs along the body surface. The barrier may be a lip-seal, and it may form a seal substantially around the reservoirs. Additionally, the electrically inert material may be of the same construction as the body of the reservoirs, or it may be a different material selected for its dielectric properties. The distance of the separation between the reservoirs may depend on the dielectric properties of the material disposed therebetween, and thus may be highly variable. In one aspect, the separation may be from about 0.05 mm to about 5 mm. In another aspect, the separation may be from about 0.1 to about 3 mm. In yet another aspect, the separation may be from about 0.2 to about 1 mm. In a side-by-side electrode assembly configuration, the distance of the separation between the reservoirs can also be used to control the depth of the penetration and the distribution of the agents in the tissue from the body surface. Depending on the configuration of the device, the electrode assemblies may also require electrical isolation from one another at the body surface in order to direct the electrical current through the tissue rather than between the reservoirs at the interface with the body surface. In one aspect, such electrical isolation can be accomplished by applying a temporary sealant between the electrical assemblies and the body surface. In addition to directing electrical current through the tissue, such a sealant may also advantageously function to temporarily affix and hold the electrode assemblies in place on the body surface. Sealants may be any useful insulative material known to one skilled in the art, for example and without limitation, gels, waxes, adhesives, impermeable polymeric or resinous materials, etc.

In another aspect, multiple electrode assemblies may be utilized to administer the active agent and the depot forming agent to the subject. As such, each electrode assembly may be coupled to the subject concurrently or consecutively. When coupled to the subject concurrently, the active agent and the depot forming agent can be administered simultaneously or consecutively. Additionally, one of the agents can be delivered continuously, while the other is delivered intermittently. Alternatively, when coupled to the subject consecutively, the first electrode assembly may be coupled to the subject to administer either the active agent or the depot forming agent. The first electrode assembly may then be replaced with the second electrode assembly to administer the remaining agent in order to cause the formation of the sustained release depot. The second electrode assembly can be coupled to the same or a different site as the first electrode assembly. Configurations having multiple electrode assemblies allow functionality similar to devices having both electrode assemblies contained therein, but also allow the ability to dynamically vary the distance between the electrodes, and thus dynamically vary the location of the in-vivo formation of the sustained release depot.

Regardless of whether a single device or multiple devices are utilized for the iontophoretic administration, various placement configurations of the electrode assemblies are contemplated. For example, in many cases side-by-side electrode assembly configurations may be beneficial. Such a configuration may allow effective iontophoresis at the target location while minimizing the extent of the movement of the electrical current in other parts of the body. This may be particularly beneficial when administering an active agent to sensitive areas such as the eye, where potential adverse effects may be caused by excessive electrical current passing through particularly sensitive tissues such as the retina in the back of the eye, the optic nerve, etc. For administrations involving the eye, in one aspect the electrode assemblies can be located side-by-side on the conjunctiva and sclera. In another aspect, one electrode assembly may be located in the inferior cul-de-sac and the other electrode assembly may be located in the superior cul-de-sac. The depot may be formed in-vivo in various tissue regions depending on the relative locations of the electrode assemblies, such as the sclera, conjunctival, subconjuctival space, ciliary body, choroids, retina, anterior chamber, vitreous, etc. The preferred site of the sustained release depot may depend on the site of drug action in the eye to provide a pharmacological effect.

While administration to nearly any portion of the eye may be suitable, in one aspect, the agents may be delivered to opposite sides of the eye using separate delivery devices. When electrical current is applied through the electrodes, the active agent and the depot forming agent are released and travel in moving fronts through their respective electrical fields. As such, the fronts will meet in a substantially central portion of the eye, resulting in the formation of a sustained release depot near the center of the globe that is distant from the vascular clearance beds of the retina and choroid. In such an embodiment, it is possible to concurrently deliver the active agent and the depot forming agent at the same time by placing the depot forming agent in the return electrode and placing both the active and return electrode on the eye, at the same time albeit separated by some distance such as in the inferior cul-de-sac and the superior cul-de-sac, respectively, and conducting iontophoresis. In another embodiment as an example, when the electrodes are placed on the pars plana next to the limbus, the site of delivery is preferably in the posterior chamber under the electrodes and the anterior chamber. When the electrodes are placed near the formix, the site of delivery is the conjunctiva and sclera under the electrodes.

Various side-by-side configurations for the electrode assemblies are possible, depending on the desired efficacy of depot formation, desired depot location, patient comfort, active agent/depot forming agent configuration, etc. In one aspect, the electrode assemblies may be placed adjacent to each other, and may be of various shapes such as, without limitation, circles, ovals, triangles, squares, rectangles, polygons, trapezoids, etc. Adjacent may include any relative orientation such as superior to inferior, lateral to medial, or any diagonal combination thereof.

In another aspect, the electrode assemblies may be of an annular configuration, and thus encircle at least a portion of the eye. Such annular electrode assemblies may be configured to nest together, and thus administer active agent and depot forming agent in close proximity within the region defined by the electrodes. For example, an outer ring electrode and an inner ring electrode may be positioned on the sclera surrounding the cornea. In one specific aspect shown in FIG. 1, an iontophoretic device 10 is shown having a first annular electrode assembly 12 having an inner radius 14. A second annular electrode assembly 16 may be located within the inner radius 14 of the first annular electrode assembly 12. In one aspect, the first and second electrodes associated with the first and second annular electrode assemblies may be annular in shape. In this specific embodiment, an outer reservoir associated with the first annular electrode assembly 12 may be of substantially the same shape as the first electrode or it may be of a different shape. Similarly, an inner reservoir associated with the second annular electrode assembly 16 may be of substantially the same shape as the second electrode or it may be of a different shape. The active agent may be contained in the first or outer reservoir and the depot forming agent may be contained in the second or inner reservoir, or the active agent may be contained in the inner reservoir and the depot forming agent may be contained in the outer reservoir. Such an annular orientation of administered active agent and depot forming agent may increase the area of interaction between the two agents while maintaining the same relative distance between the reservoirs of the two agents, and thus increase the efficacy of the in-vivo formation of the sustained release depot.

Figure 2:
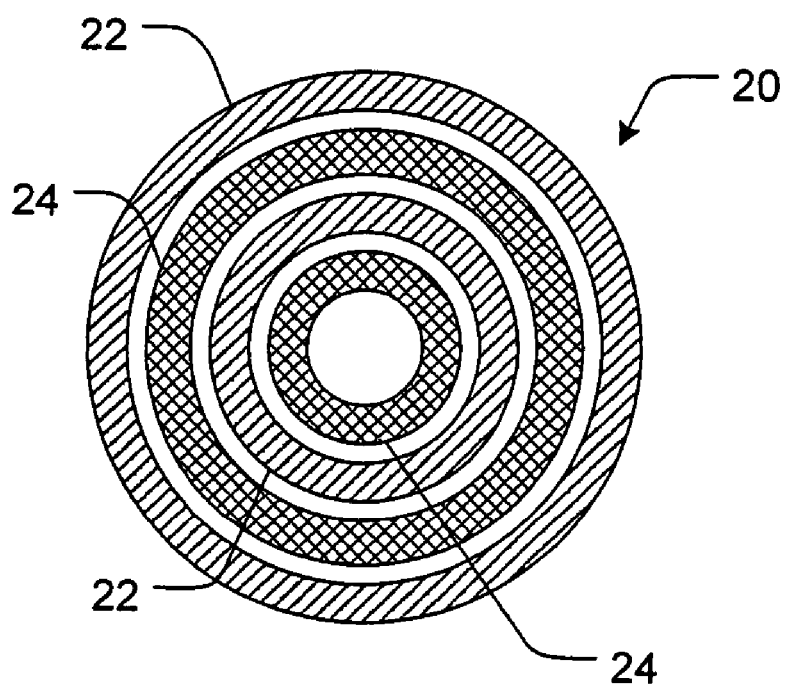
FIG. 2 is a front view of an iontophoretic device in accordance with another aspect of the present invention.

In yet another specific aspect, multiple active agent and depot forming agent electrode assemblies may be utilized to further increase the area of agent interaction and the efficacy of the in-vivo formation of the sustained release depot. FIG. 2 shows an iontophoretic device 20 having multiple electrode assemblies 22, 24 arranged in a concentric "bullseye" pattern. In one aspect, it may be beneficial for the reservoirs associated with the electrode assemblies to contain either active agent or depot forming agent in an alternating configuration. For example, reservoirs associated with electrode assemblies labeled 22 may contain active agent, and reservoirs associated with electrode assemblies labeled 24 may contain depot forming agent, and vice versa. Each electrode assembly may be couple to a single electrode or to a single electrical current source, or multiple electrode assemblies can be coupled to a single electrode or to a single electrical current source. It should be noted that in other aspects, the arrangement of multiple electrode assemblies need not be in an alternating configuration with respect to the active agent and the depot forming agent, but may be any configuration known to one skilled in the art. Additionally, numerous configurations including more than two electrode assemblies are contemplated, all of which are considered to be within the scope of the present invention. For example, a single electrode assembly containing an active agent can be associated with multiple electrode assemblies containing a depot forming agent or multiple depot forming agents. Similarly, a single electrode assembly containing a depot forming agent can be associated with multiple electrode assemblies containing an active agent or multiple active agents.

Figure 3:
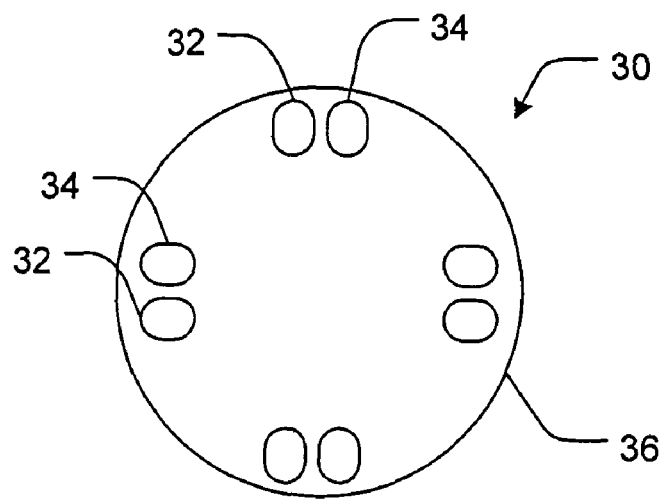
FIG. 3 is a front view of an iontophoretic device in accordance with yet another aspect of the present invention.

In a further aspect of the present invention, FIG. 3 shows an example of an ocular iontophoretic device 30 having multiple non-annular electrode assemblies. The device 30 may include a substrate 36 having a plurality of electrode assemblies containing either active agent 32 or depot forming agent 34. Any number or spatial orientation of electrode assemblies is intended to be included within the scope of the present invention. FIG. 3 is merely intended to show that various side-by-side electrode configurations are possible.

The reservoirs according to aspects of the present invention are designed to hold either an active agent or a depot forming agent prior to administration through the body surface of a subject. In one aspect, the reservoirs are distinct, having lumens that are completely separate from one another. Additionally, a reservoir may contain at least one access port to allow the reservoir to be filled while in contact with the body surface of the subject. This configuration may allow the reservoir to be filled during use as the agent within is depleted. Various iontophoretic reservoir materials are known to those skilled in the art, and all are considered to be within the scope of the present invention.

Additional electrodes for immediate release of the active agent without the involvement of the depot forming agent can be operated concurrently with the side-by-side active-agent and depot-forming agent electrode. For ocular delivery, this additional electrode is placed on the eye surface away from the vicinity of the side-by-side electrodes. The additional electrode will provide a "burst" of the active agent for an initial high dose treatment of the disease with iontophoresis. A burst of the depot forming agent for more effective in-vivo interactions between the active agent and the depot forming agent can also be provided under this setting. Another electrode to serve as a return electrode on a body surface away from the eye, e.g., on the face, can also be used in conjunction with the side-by-side electrodes and the immediate release electrodes on the eye. A dose controller as the electrical current source controlling the electric current applied across the electrodes can be programmed to provide different dosing intervals for both the active agent and the depot forming agent from the side-by-side electrodes and these auxiliary electrodes. This system allows the switching back and forth of the electric current across these electrodes to control the delivery of the active agent and the depot forming agents and reduce the duration of the electric current passage to minimize possible adverse effects due to the application of the electric current. Different electric current protocols can be carried out utilizing these electrodes to provide effective immediate and sustained release of the active agent.

The electrodes of the present invention are designed to deliver electrical current across the associated reservoirs to iontophoretically deliver the agent located therein. The electrodes can be of any material or manufacture known to one skilled in the art. Various examples include metal electrodes, conductive glass electrodes, etc. A single electrode may be coupled to a single reservoir or to multiple reservoirs depending on the particular configuration of a given electrode assembly. Additionally, in some aspects of the present invention, an electrode may also be a reservoir, with the depot forming agent being delivered from the body of the electrode.

For optimal iontophoretic delivery of active agents, excipients, and depot forming agents into the eye, a permselective material may be placed in ion-conducting relation to the eye surface. An electric current of AC, DC, and AC with superimposed DC can be used to transport the compound of interest through the permselective material into the eye. The permselective material is capable of hindering iontophoretic transport of a competing ion and increases the transference efficiency of the compound of interest during iontophoresis. As a result, the invention allows the compound of interest to be delivered iontophoretically into the eye more efficiently than iontophoresis without the permselective material. For example, more efficient iontophoretic transport can be achieved by placing the permselective material against the current driving electrode (e.g., Ag/AgCl) between the electrode and the reservoir chamber to prevent the products of electrochemical reactions generated at the electrode surface (e.g., Ag or Cl ions) from moving into the reservoir. Another example is to place the permselective material between the body surface and the reservoir to prevent the migration of the active agent and endogenous ions into depot forming agent reservoir or vice versa the depot forming agent and endogenous ions into the active agent reservoir during iontophoresis. Any permselective material capable of hindering iontophoretic transport of a competing ion during iontophoretic transport of the compound of interest may be used in conjunction with the invention. The permselective material may be provided in any of a number of forms as described in applicant's copending U.S. patent application Ser. No. 10/371,148 entitled "METHODS AND SYSTEMS FOR CONTROLLING AND/OR INCREASING IONTOPHORETIC FLUX", filed on Feb. 21, 2003, which is incorporated herein by reference. For example, the material may be provided in a liquid, partially liquid, gelled, partially solid, or fully solid state. In some instances, the permselective material may be supported by a support structure such as an additional membrane having sufficient porosity and chemical inertness so as to avoid interfering with the performance of the permselective material, yet having sufficient mechanical integrity for ease in handling. The material can also be provided in the form of a membrane having a surface sized and/or shaped for direct contact with the eye or shaped for direct contact with the current driving electrode (e.g., Ag/AgCl). In other instances, the permselective material may be comprised of a polyelectrolyte, which can be a single molecule or an aggregate of molecules having ions or ionizable groups.

As will be recognized, the noninvasive delivery mechanism may be selected from a wide variety of suitable mechanisms known in the art, such as iontophoretic delivery. In one aspect, the administration may be to a subject's eye. In other aspects, the noninvasive delivery mechanism can be related to patches, topical ointments, sonophoresis, electroporation, such as those used in either ocular and or transdermal delivery. The specific mechanism may be selected in part based on suitability for administration to the target physiological area of a subject's body. Furthermore, it should be noted that the active agent and depot forming agent may be administered using a single route, or different routes to arrive at the site of action. In such cases, either the drug or the depot forming agent may be delivered through an alternate route as compared to the other. In the case where a single route is used, the administration may be made using a single device that properly accommodates both agents, or may be delivered from separate devices. In the case of separate or different routes of administration, nearly always, multiple or separate devices will be used. Additionally, iontophoretic and sonophoretic methods may be assisted by perturbing an application situs prior to administration. Such perturbation may include treatment by microneedle, heat, laser, etc.

In addition to the noninvasive iontophoretic mechanisms discussed above, minimally invasive procedures are also contemplated for the delivery of the active agent and/or the depot forming agent into tissues of the subject, including the eye. One example of a minimally invasive administration method may include periocular injections

EXAMPLES

The following examples are intended to be merely illustrative of the various aspects of the invention disclosed herein and are not intended in any way to limit the scope of the claimed invention. Other aspects of the invention that are considered equivalent by those skilled in the art are also within the scope of this invention.

Example 1

Table 1 shows the bench top experiments performed to test the solubility of dexamethasone phosphate (DexP) and zinc (Zn) ion. In this example, zinc ion was the depot forming agent and DexP was the active agent.

TABLE 1

Concentration of Zn ion

| DexP | 0.1M | 0.05M | 0.01M | 0.005M | 0.001M |
|---|---|---|---|---|---|
| 0.05M | Precipitation | Precipitation | Precipitates | Turbid, settles on standing | Slightly turbid |
| 0.01M | Small amount precipitates | Turbid, settles within few minutes | Turbid, settles on standing for some time | Stays turbid for long time | Slightly turbid |
| 0.005M | Turbid, settles on standing for several minutes | Turbid, settles slowly, very little solid material | Turbid but settles slowly | Slight turbidity, doesn't settle | Clear solution |
| 0.001M | Slightly turbid, no tendency to settle (almost clear) | Clear solution | Clear solution | Clear solution | Clear solution |

Bench top experiments were also performed with DexP and ferrous (Fe) ion (Table 2).

Example 2

In this example, ferrous ion was the depot forming agent and DexP was the active agent.

TABLE 2

Concentration of Ferrous Ion

| DexP | 0.1M | 0.05M | 0.01M | 0.005M | 0.001M |
|---|---|---|---|---|---|
| 0.05M | Precipitation | Precipitation | Very turbid and stays turbid for several minutes before settling | Turbid, stays long time without settling | Clear, no turbidity appears. |
| 0.01M | Turbid, but settles down | Turbid, settles on standing | Turbid, do not settle in 30 min. | Stays turbid even after 1 hr | Clear, no turbidity appears |
| 0.005M | Turbid, settles on standing for several minutes | Turbid, settles slowly, takes an hour or more | Turbid and stays so without settling | Slight turbidity, doesn't settle | Clear, no turbidity appears |
| 0.001M | Slight turbidity, no tendency to settle | Foggy, not clear solution | Foggy, not a clear solution | Foggy, not fully clear solution | Clear, no turbidity appears |

In yet another example, the solubility of DexP and calcium (Ca) ion was studied. Calcium ion was the depot forming agent and DexP was the active agent. It was discovered that mixing a solution of DexP disodium salt ($\geqq 0.005$ M) and solution of $CaCl_2$ ($\geqq 0.005$ M) formed a gel.

Figure 4:
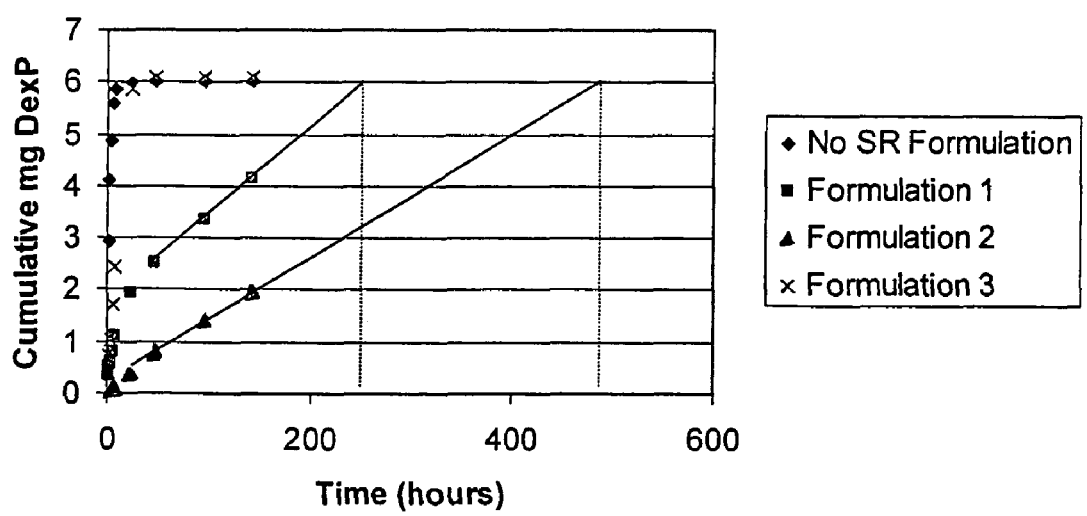
FIG. 4 is a graphical representation of the dissolution profiles of three depot formulations in accordance with various embodiments of the present invention as compared to the dissolution profile for a control.

In another study, the dissolution of dexamethasone phosphate (DexP) from different forms of precipitation (ZnDexP, SnDexP, and CaDexP) as depot was monitored in dialysis membrane systems. FIG. 4 shows the dissolution profiles of these three formulations (depot forming agents, Zn, Sn, Ca as Formulations 1, 2, and 3, respectively) and the control (DexP formulation without depot forming agents; no sustained-release (SR) formulation). The results in FIG. 4 suggest that the method of precipitation between the depot forming agents and the active agent can provide slow and sustained drug delivery for more than a week.

Example 3

This example provides evidence of non-invasive delivery of a sustained release system to the eye for ocular drug delivery in rabbits in-vivo. In this study, an ocular device of side-by-side active and depot forming agent chambers (similar to that in FIG. 3) was placed on the eyes of rabbits. The electrode chambers of the device were positioned on the conjunctiva near the pars plana. The active and depot forming agents were 0.5 M triamcinolone acetonide phosphate and 1.0 M dodecyl ammonium, respectively. The delivery of the sustained release system was achieved by applying a constant direct electric current of two milliampere across the side-by-side chambers for 15 minutes, in which the active agent was delivered from the cathode and the depot forming agent was from the anode. For comparison, iontophoretic delivery of triamcinolone acetonide phosphate without the depot forming agent, dodecyl ammonium, was conducted as the control. Six groups of 2 to 3 rabbits with each group assigned to the different time point (10-min, 4-hour, or 1-day) and different protocol (conventional iontophoresis control or sustained release iontophoresis) were used. At 10 minutes, 4 hours, and 1 day after the iontophoresis applications, the animals were euthanized and the eyes were enucleated for triamcinolone acetonide and triamcinolone acetonide phosphate assays. The assay procedure involved extracting these compounds from the conjunctiva, sclera, and vitreous humor with a pH-adjusted organic solvent and HPLC analysis. The amounts of the active agent in the eye after the iontophoresis applications are shown in Table 3. The results in the table suggest that the present invention provides a sustained release system compared to that of conventional ocular iontophoresis.

TABLE 3

Total amounts of triamcinolone acetonide and triamcinolone acetonide phosphate in the eye.

| | Sustained release system delivered by iontophoresis | Conventional iontophoresis |
|---|---|---|
| 10 min | 0.7 mg | 0.4 mg |
| 4 hours | 0.2 mg | 0.01 mg |
| 24 hours | 0.02 mg | 0 mg |

It should be understood that the above-described arrangements are only illustrative of the application of the principles of the present invention. Numerous modifications and alternative arrangements may be devised by those skilled in the art without departing from the spirit and scope of the present invention. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of providing sustained in-vivo release of an active agent in a subject comprising:
   delivering the active agent noninvasively to the subject;
   delivering a depot forming agent noninvasively to the subject, wherein the active agent and the depot forming agent are delivered from a single device;
   reacting the active agent with the depot forming agent inside the subject to cause a reduction in solubility of the active agent to form a precipitate of the active agent and thus create an active agent sustained release depot; and
   allowing the depot to release the active agent over a sustained period of time.

2. The method of claim 1, wherein the reaction is an ionic association between the active agent and the depot forming agent.

3. The method of claim 2, wherein the depot forming agent is polyvalent and has multiple charges that are opposite to charges carried by the active agent.

4. The method of claim 3, wherein the precipitate of depot forming agent and active agent has a ratio of depot agent to active agent of from about 4:1 to about 1:4.

5. The method of claim 1, wherein the depot forming agent is administered either prior to, concurrently with, or following the active agent.

6. The method of claim 5, wherein the depot forming agent is administered concurrently with the active agent.

7. The method of claim 1, wherein the depot forming agent is administered by the same route as the active agent.

8. The method of claim 1, wherein the depot forming agent is administered by a different route than the active agent.

9. The method of claim 1, wherein the sustained release depot comprises a crystal, a gel, a semi-solid, a liquid having a viscosity that is higher than a viscosity of the active agent prior to reaction with the depot forming agent, or a combination thereof.

10. The method of claim 1, wherein the active agent is a member selected from a group consisting essentially of: analeptic agents, analgesic agents, anesthetic agents, antiasthmatic agents, antiarthritic agents, anticancer agents, anticholinergic agents, anticonvulsant agents, antidepressant agents, antidiabetic agents, antidiarrheal agents, antiemetic agents, antihelminthic agents, antihistamines, antihyperlipidemic agents, antihypertensive agents, anti-infective agents, antiinflammatory agents, antimigraine agents, antineoplastic agents, antiparkinsonism drugs, antipruritic agents, antipsychotic agents, antipyretic agents, antispasmodic agents, antitubercular agents, antiulcer agents, antiviral agents, anxiolytic agents, appetite suppressants, attention deficit disorder and attention deficit hyperactivity disorder drugs, cardiovascular agents including calcium channel blockers, antianginal agents, central nervous system ("CNS") agents, beta-blockers and antiarrhythmic agents, central nervous system stimulants, diuretics, genetic materials, hormonolytics, hypnotics, hypoglycemic agents, immunosuppressive agents, muscle relaxants, narcotic antagonists, nicotine, nutritional agents, parasympatholytics, peptide drugs, psychostimulants, sedatives, steroids, smoking cessation agents, sympathomimetics, tranquilizers, vasodilators, β-agonists, and tocolytic agents, and mixtures thereof.

11. The method of claim 1, wherein the active agent is a member selected from the group consisting essentially of: steroids, aminosteroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides, and mixtures thereof.

12. The method of claim 1, wherein the active agent is used to treat an eye disease selected from the group consisting of: macular edema, age related macular degeneration, anterior, intermediate, and posterior uveitis, HSV retinitis, diabetic retinopathy, bacterial, fungal, or viral endophthalmitis, eye cancers, glioblastomas, glaucoma, and glaucomatous degradation of the optic nerve.

13. The method of claim 1, wherein the depot forming agent is a member selected from the group consisting essentially of: inorganic ions, organic cations, organic anions, and ionic pharmaceutical excipients.

14. The method of claim 1, wherein the depot forming agent is a member selected from the transition metals in the periodic tables.

15. The method of claim 1, wherein the depot forming agent is an ion selected from the group consisting of: $Ca^{2+}$, $Sn^{2+}$, $Fe^{2+}$, $Fe^{3+}$, $Mn^{2+}$, $Mg^{2+}$, $Zn^{2+}$, $NH_4^+$, $PO_4^{3-}$, $CO_3^{2-}$, $SO_4^{2-}$.

16. The method of claim 1, wherein the depot forming agent has an adequate ionic charge for both effective iontophoretic delivery and effectively reacting with the active agent to form the sustained release depot.

17. The method of claim 1, further comprising restricting in-vivo movement of the active agent for a time sufficient to allow reaction with the depot forming agent and formation of the sustained release depot.

18. The method of claim 17, wherein restricting the in-vivo movement is accomplished by constriction of blood vessels exiting an area in which active agent precipitation occurs.

19. The method of claim 18, wherein constriction of blood vessels is induced by application of physical force to the blood vessels.

20. The method of claim 18, wherein the constriction of blood vessels is induced by administration of a vasoconstricting agent.

21. The method of claim 20, wherein the vasoconstricting agent is a member selected from the group consisting of α-agonists such as naphazoline, and tetrahydrozoline, sympathomimetics such as phenylethylamine, epinephrine, norepinephrine, dopamine, dobutamine, colterol, ethylnorepinephrine, isoproterenol, isoetharine, metaproterenol, terbutaline, metearaminol, phenylephrine, tyramine, hydroxyamphetamine, ritrodrine, prenalterol, methoxyamine, albuterol, amphetamine, methamphetamine, benzphetamine, ephedrine, phenylpropanolamine, methentermine, phentermine, fenfluramine, propylhexedrine, diethylpropion, phenmetrazine, and phendimetrazine.

22. The method of claim 20, wherein the vasoconstrictor is passively delivered to the tissue.

23. The method of claim 20, wherein the vasoconstrictor is administered either before, or concurrently with administration of the active agent.

24. The method of claim 23, wherein the vasoconstrictor has the same polarity as the depot forming agent.

25. The method of claim 1, further comprising sealing an application situs through which the active agent was delivered with a sealant.

26. The method of claim 25, wherein the sealant is a member selected from the group consisting of: gels, glues, and impermeable polymeric or resinous membranes.

27. The method of claim 1, wherein the non-invasive administration is either iontophoretic, sonophoretic, or electroporation administration.

28. The method of claim 27, wherein the non-invasive administration is iontophoretic.

29. The method of claim 1, wherein the sustained release depot provides either local or systemic delivery of the active agent.

30. The method of claim 1, wherein the active agent is administered to the subject's eye.

31. The method of claim 1, wherein the depot forming agent and active agent are delivered side-by-side next to each other to a subject's eye.

32. The method of claim 1, wherein either the active agent or the depot forming agent is passively delivered to the tissue.

33. A medicinal depot formulation in a subject formed by the method of claim 1, comprising:
 a mass of the active agent in precipitated form which becomes solubilized and releases active agent over a sustained period of time.

* * * * *